(12) United States Patent
Holzer

(10) Patent No.: US 11,582,996 B2
(45) Date of Patent: Feb. 21, 2023

(54) PLANT EXTRACTS AND THERAPEUTIC COMPOUNDS IN SMOKING UTENSILS AND IN HONEY COMPLEXES

(71) Applicant: STICKIT LTD, Ra'anana (IL)

(72) Inventor: Asher Holzer, Raanana (IL)

(73) Assignee: STICKIT LTD., Ra'anana (IL)

(*) Notice: Subject to any disclaimer, the term of this patent is extended or adjusted under 35 U.S.C. 154(b) by 0 days.

(21) Appl. No.: 17/158,360

(22) Filed: Jan. 26, 2021

(65) Prior Publication Data
US 2021/0145043 A1    May 20, 2021

Related U.S. Application Data

(63) Continuation-in-part of application No. PCT/IL2019/050846, filed on Jul. 25, 2019.
(Continued)

(51) Int. Cl.
*A24D 1/00* (2020.01)
*A61K 9/00* (2006.01)
(Continued)

(52) U.S. Cl.
CPC .............. *A24D 1/002* (2013.01); *A01K 47/06* (2013.01); *A24D 1/18* (2013.01); *A61K 9/007* (2013.01); *A61K 31/045* (2013.01); *A61K 31/352* (2013.01)

(58) Field of Classification Search
CPC .... A61K 31/045; A61K 9/007; A61K 31/352; A24B 15/284; A24B 15/282;
(Continued)

(56) References Cited

U.S. PATENT DOCUMENTS 2,072,361 A    3/1937  Ehrig et al.
6,730,330 B2*  5/2004  Whittle ................. A61K 9/006
                                                424/435
(Continued)

FOREIGN PATENT DOCUMENTS

CN    204362945       6/2015
DE      1873551       6/1963
DE    202004009457   11/2004
WO    2017103795 A1   6/2017

OTHER PUBLICATIONS

International Search Report dated Nov. 14, 2019 for PCT Application No. PCT/IL2019/050846.

*Primary Examiner* — Jianfeng Song
(74) *Attorney, Agent, or Firm* — The Roy Gross Law Firm, LLC; Roy Gross

(57) ABSTRACT

Methods and utensils are provided for administering plant extract(s) at controlled amount via smoking, as well as for providing complexes of honey and plant extracts. Plant extract(s) may be used in utensils that are inserted into a smoking appliance, and have indications of the compounds and/or characteristics of the plant extract. Upon smoking the smoking appliance, the plant extracts may be inhaled in pre-defined amounts. Using plant extracts in such way enables standardization of amounts and components thereof, and may be particularly applicable to cannabis oils. Furthermore, complexes of honey and plant extracts may be provided by letting bees step on or be soiled by plant extracts on their way into the beehive, causing them to incorporate the plant extracts into the honey preparation process. Resulting complexes may be a preferable and particularly beneficial way of administering plant extracts, e.g., cannabis extracts.

6 Claims, 4 Drawing Sheets

Related U.S. Application Data

(60) Provisional application No. 62/723,001, filed on Aug. 27, 2018, provisional application No. 62/703,657, filed on Jul. 26, 2018.

(51) Int. Cl.
| | | |
|---|---|---|
| *A61K 31/045* | (2006.01) | |
| *A61K 31/352* | (2006.01) | |
| *A24D 1/18* | (2006.01) | |
| *A01K 47/06* | (2006.01) | |

(58) Field of Classification Search
CPC ....... A24B 15/303; A01K 47/06; A24F 25/00; A24D 1/002; A24D 1/18
See application file for complete search history.

(56) References Cited

U.S. PATENT DOCUMENTS

| | | | |
|---|---|---|---|
| 9,220,298 B1 | 12/2015 | En'Wezoh et al. | |
| 2008/0029106 A1* | 2/2008 | Mishra | A24D 3/061 131/365 |
| 2016/0037823 A1* | 2/2016 | Ruben | A24D 3/061 131/337 |
| 2017/0273349 A1* | 9/2017 | Moore | A24B 15/16 |
| 2017/0347701 A1 | 12/2017 | Pitta | |
| 2018/0360103 A1* | 12/2018 | Kaplan | D21H 21/16 |
| 2019/0261681 A1* | 8/2019 | Playford | A24F 23/02 |

* cited by examiner

150

```
┌─────────────────────────────────────────────────────────────┐
│   ADMINISTERING A PLANT EXTRACT AT A CONTROLLED AMOUNT      │─ 152
└─────────────────────────────────────────────────────────────┘
                              │
┌─────────────────────────────────────────────────────────────┐
│     ADMINISTERING THERAPEUTIC COMPOUND(S) AT A CONTROLLED   │─ 153
│                           AMOUNT                            │
└─────────────────────────────────────────────────────────────┘
                              │
┌─────────────────────────────────────────────────────────────┐
│   APPLYING THE PLANT EXTRACT(S) AND OR THERAPEUTIC          │
│   COMPOUND(S) TO A UTENSIL THAT IS DESIGNED TO BE INSERTED  │─ 155
│                 INTO A SMOKING APPLIANCE                    │
└─────────────────────────────────────────────────────────────┘
                              │
┌─────────────────────────────────────────────────────────────┐
│   DESIGNING THE UTENSIL TO BE INSERTED INTO THE SMOKING     │─ 157
│                    APPLIANCE BY STICKING                    │
└─────────────────────────────────────────────────────────────┘
                              │
┌─────────────────────────────────────────────────────────────┐
│   MAKING THE UTENSIL A STICK THAT IS THINNER THAN THE       │
│   CIGARETTE AND HAS A SHARP END CONFIGURED TO BE INSERTED   │─ 158
│                INTO TOBACCO OF THE CIGARETTE                │
└─────────────────────────────────────────────────────────────┘
                              │
┌─────────────────────────────────────────────────────────────┐
│    INDICATING COMPOUND(S) THAT ARE INCLUDED IN THE PLANT    │─ 160
│                    EXTRACT ON THE UTENSIL                   │
└─────────────────────────────────────────────────────────────┘
                              │
┌─────────────────────────────────────────────────────────────┐
│   USING THE SMOKING APPLIANCE TO INHALE THE PLANT EXTRACT(S)│
│   AND/OR THERAPEUTIC COMPOUND(S) FROM THE UTENSIL INSERTED  │─ 170
│                         THEREWITHIN                         │
└─────────────────────────────────────────────────────────────┘
                              │
┌─────────────────────────────────────────────────────────────┐
│    PROVIDING A PLURALITY OF UTENSILS WITH DIFFERENT LEVELS  │─ 180
│         AND/OR COMBINATIONS OF THE INDICATED COMPOUND       │
└─────────────────────────────────────────────────────────────┘
                              │
┌─────────────────────────────────────────────────────────────┐
│   INDICATING A THC LEVEL AND PREDOMINANT COMPONENT(S) OF    │─ 182
│      CANNABIS EXTRACT/OIL AS THE PLANT EXTRACT              │
└─────────────────────────────────────────────────────────────┘
                              │
┌─────────────────────────────────────────────────────────────┐
│  PROVIDING A PLURALITY OF UTENSILS WITH DIFFERENT LEVELS OF │─ 185
│     THC AND/OR WITH DIFFERENT PREDOMINANT COMPONENTS        │
└─────────────────────────────────────────────────────────────┘
```

*Figure 4*

PLANT EXTRACTS AND THERAPEUTIC COMPOUNDS IN SMOKING UTENSILS AND IN HONEY COMPLEXES

CROSS-REFERENCE TO RELATED APPLICATIONS

This application is a continuation-in-part of PCT International Application No. PCT/IL2019/050846, International Filing Date Jul. 25, 2019, claiming the benefit of U.S. Patent Applications Nos. 62/703,657, filed Jul. 26, 2018, and 62/723,001, filed Aug. 27, 2018, which are hereby incorporated by reference.

BACKGROUND OF THE INVENTION

1. Technical Field

The present invention relates to the field of processing plant extracts and/or therapeutic compounds, and more particularly, to using plant extracts and/or therapeutic compounds in smoking utensils and in honey complexes.

2. Discussion of Related Art

Plant extracts and therapeutic compounds are being used in a range of methods, some of which being disadvantageous with respect to the form, efficiency and predictability of the administered compounds.

SUMMARY OF THE INVENTION

The following is a simplified summary providing an initial understanding of the invention. The summary does not necessarily identify key elements nor limit the scope of the invention, but merely serves as an introduction to the following description.

One aspect of the present invention provides a method of administering a plant extract at a controlled amount, the method comprising: applying the plant extract to a utensil that is designed to be inserted into a smoking appliance, indicating at least one compound that is included in the plant extract on the utensil, and using the smoking appliance to inhale the plant extract from the utensil inserted therewithin.

One aspect of the present invention provides a method of administering at least one therapeutic compound at a controlled amount, the method comprising: applying the at least one therapeutic compound to a utensil that is designed to be inserted into a smoking appliance, and using the smoking appliance to inhale the at least one therapeutic compound from the utensil inserted therewithin.

One aspect of the present invention provides a utensil comprising plant extract(s) and/or therapeutic compound(s) and optionally indication(s) of the extract(s), compounds thereof and/or therapeutic compound(s) in the utensil, wherein the utensil is designed to be inserted into a smoking appliance and release the plant extract(s) and/or therapeutic compound(s) upon smoking the smoking appliance.

One aspect of the present invention provides a method comprising deriving a complex of honey and a plant extract by applying the plant extract onto a substrate and attaching the substrate onto at least one hive region that is stepped on by bees, wherein the applying and the substrate are configured to soil bees that step on the substrate by the plant extract, and wherein the complex is collected from the hive.

One aspect of the present invention provides a substrate infused with a plant extract that is attachable onto at least one hive region that is stepped on by bees, wherein the substrate is configured to soil bees that step thereon by the plant extract.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings:

FIG. 4 is a high-level flowchart illustrating a method of administering a plant extract or any compound at a controlled amount, according to some embodiments of the invention.

DETAILED DESCRIPTION OF THE INVENTION

Figure 1:
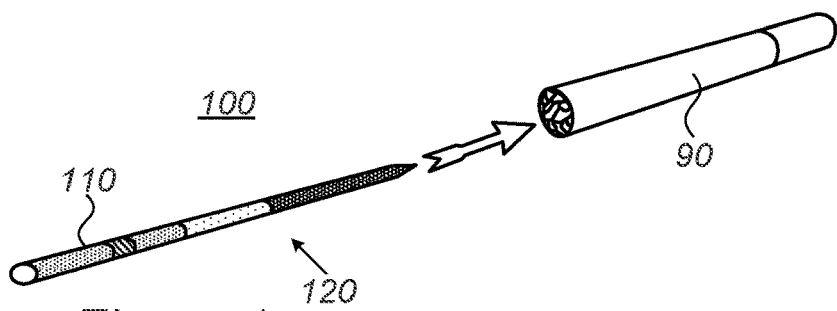
FIGS. 1-3 are schematic illustrations of systems, utensils and packaged sets thereof, according to some embodiments of the invention.

In the following description, various aspects of the present invention are described. For purposes of explanation, specific configurations and details are set forth in order to provide a thorough understanding of the present invention. However, it will also be apparent to one skilled in the art that the present invention may be practiced without the specific details presented herein. Furthermore, well known features may have been omitted or simplified in order not to obscure the present invention. With specific reference to the drawings, it is stressed that the particulars shown are by way of example and for purposes of illustrative discussion of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that may be practiced or carried out in various ways as well as to combinations of the disclosed embodiments. Also, it is to be understood that the phraseology and terminology employed herein are for the purpose of description and should not be regarded as limiting.

Embodiments of the present invention provide efficient and economical methods and mechanisms for using plant extracts and/or therapeutic compounds, and thereby provide improvements to the technological field of administering plant extracts and/or therapeutic compounds, with an emphasize on cannabis extracts and oils and related compounds. Methods and utensils are provided for administering plant extract(s) and/or therapeutic compound(s) at controlled amounts via smoking, as well as for providing complexes of honey and plant extracts and/or therapeutic compound(s). Plant extract(s) and/or therapeutic compound(s) may be used in utensils that are inserted into a smoking appliance, and have indications of the compounds and/or characteristics of the plant extract(s) and/or therapeutic compound(s). Upon smoking, using the smoking appliance, the plant extract(s) and/or therapeutic compound(s) may be inhaled in pre-defined amounts.

Using plant extract(s) and/or therapeutic compound(s) in such way enables standardization of amounts and components thereof, and may be particularly applicable to cannabis oils. Furthermore, complexes of honey and plant extract(s) and/or therapeutic compound(s) may be provided by letting bees step on or be soiled by plant extract(s) and/or therapeutic compound(s) on their way into the beehive, causing them to incorporate the plant extract(s) and/or therapeutic compound(s) into the honey preparation process. Resulting complexes may be a preferable and particularly beneficial way of administering plant extract(s) and/or therapeutic compound(s), e.g., cannabis extracts. It is noted that the term "plant extract" is used in a broad sense, as any substance or compositions of substances that are removed from plant tissues, namely extracted therefrom, by various technical means. Plant extracts, as used herein, may include extracts from multiple plant species, and may include multiple extract from the same plant species which are achieved using different methods, or combinations thereof Plant extracts may also be augmented or enriched with synthetic compounds, either ones that are present in the plant extract or additives. In particular, plant extracts may comprise therapeutic compounds of various sources.

Figure 2:
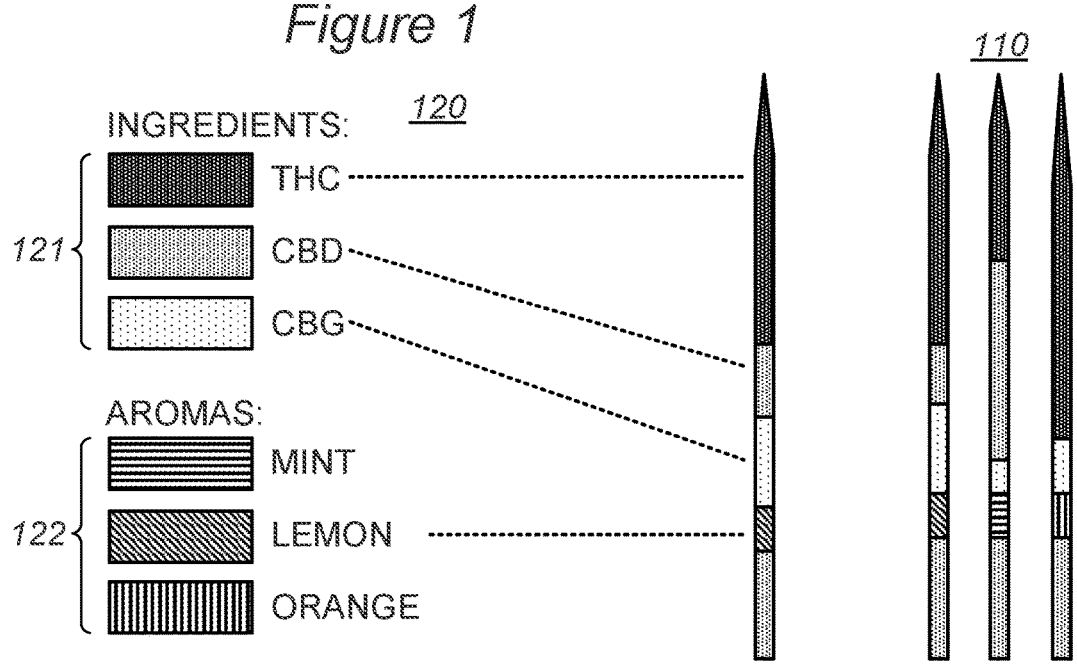
Figure 3:
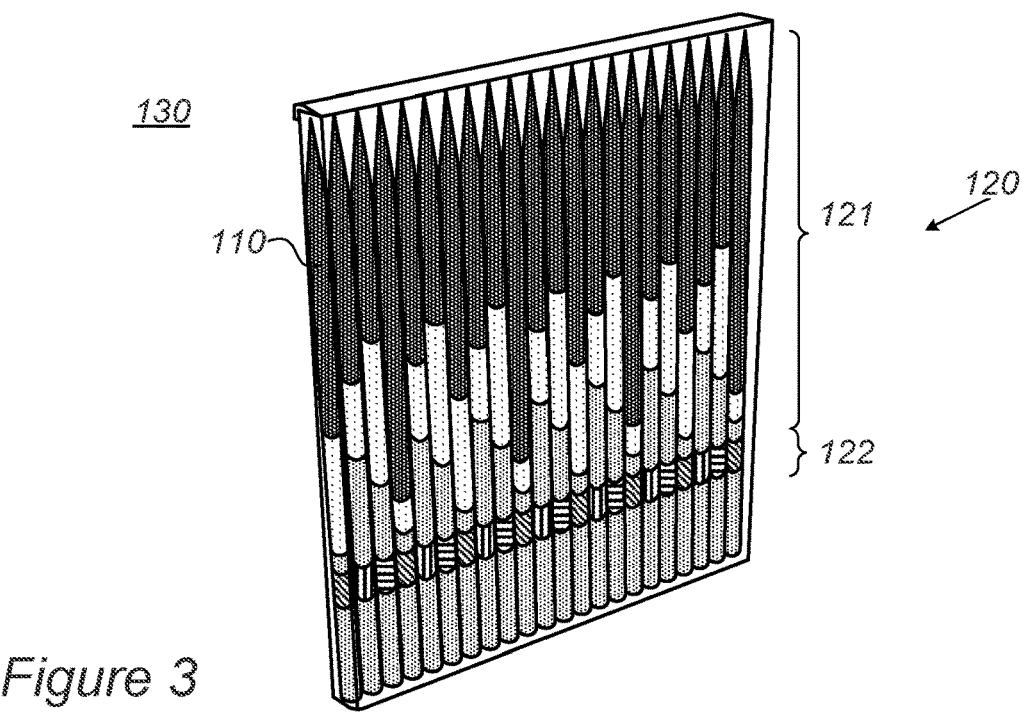

FIGS. 1-3 are schematic illustrations of systems 100, utensils 110 and packaged sets 130 thereof, according to some embodiments of the invention.

Utensils 110 may comprise plant extract(s) comprising at least one compound, and an indication 120 of the at least one compound; utensils 110 being designed to be inserted into a smoking appliance 90 and release the plant extract(s) upon smoking of smoking appliance 90. For example, smoking appliance 90 may comprise cigarette and utensil 110 may comprise a stick that is thinner than cigarette 90 and has a sharp end configured to be inserted (e.g., sticked, impaled, pushed) into tobacco of cigarette 90 throughout most of a length of cigarette 90. Systems 100 for delivery of plant extracts comprise smoking appliance 90 with inserted utensil(s) 110.

Upon use, utensils 110 may be burned to release the plant extract, or may remain at least partly intact upon releasing the plant extract. The rate of burning and/or releasing of the plant extract may be determined by the structure and composition of utensils 110 with respect to typical burning profiles of smoking appliance 90—providing a specified profile of released compound concentrations and/or amounts. For example, the burning rate, or compound release rate may be similar to the burning rate of the tobacco blend, possibly in relation to burn rates of different blends and/or different types of smoking appliance 90. In certain embodiments, utensils 110 may be made of porous material. The porous material may provide a burning rate of utensil 110 that depends on the rate of air flow therethrough, possibly similar to the variable burning rate of a smoked cigarette, which depends on the intensity of air flow therethrough.

In certain embodiments, utensils 110 may comprise therapeutic compound(s), possibly at different amounts or combinations. Utensils 110 may be designed to be inserted into smoking appliance 90 and release the therapeutic compound(s) upon smoking of smoking appliance 90. For example, smoking appliance 90 may comprise cigarette and utensil 110 may comprise a stick that is thinner than cigarette 90 and has a sharp end configured to be inserted into tobacco of cigarette 90 throughout most of a length of cigarette 90. Systems 100 for delivery of therapeutic compound(s) comprise smoking appliance 90 with inserted utensil(s) 110.

In certain embodiments, the therapeutic compound(s) may comprise synthetic compounds that are similar to compounds found in plant extracts, and therapeutic compound(s) may be added to plant extract(s) in utensil 110. For example, synthetic cannabinoids may be added to utensil 110 with cannabis oil as the plant extract.

According to some embodiments, utensils 110 may be configured to burn and/or release the plant extract at approximately the same rate as the tobacco burn rate of smoking appliance 90 into which it is to be inserted. According to some embodiments, the combustion rate and/or plant extract release rate of utensil 110 may be determined according to the materials from which it is prepared, coatings with which it is coated and the like, as well as a level of porosity of utensil 110 or components of specified mixes of burning materials of which utensil 110 is made, that may be adjusted to determine the burning rate of utensil 110. Accordingly, different grades of utensils 110 may be prepared, each of which may have a different combustion rate.

Indication(s) 120 may provide information concerning the composition and/or amount of plant extract(s) and/or compound(s) thereof in a way that is standardized. For example, indication(s) 120 may be configured to provide an inhaled amount of the compounds when using utensil 110 with smoking appliance 90 (e.g., in terms of amounts of THC, tetrahydrocannabinol, per cigarette). For example, utensil 110 usable in one smoking appliance 90, may include a pre-defined amount and/or composition of plant extract which is released during the smoking of one smoking appliance 90 with utensil 110 used therein. Indications 120 thus provide a highly controllable way of consuming plant extract(s) and/or compound(s) while smoking. For example, indications 120 illustrated schematically in FIGS. 1 and 2 may comprise color coded regions along stick-like utensil 110.

Utensils 110 may be shaped in various ways that allow their insertion into smoking appliance 90 and provide effective release of the plant extract, possibly to provide the smoker with specified amounts of the at least one compound. Utensils 110 may be stick-like and be configured to be insertable into any smoking appliance 90, e.g., a cigarette, a cigar or any other smoking article. Utensils 110 may be made of any material which is safe to be smoked with into smoking appliance 90, insertable thereto, and able to receive, absorb and upon smoking release the plant extract and/or compounds thereof. Utensils 110 may be sufficiently rigid to be inserted into a conventional cigarette and at the same time, not be brittle to prevent its breaking when inserted into the conventional cigarette, a cigar or any other smoking article.

In certain embodiments, smoking appliance 90 may comprise various herbs other than tobacco, or possibly any other medium that may be configured to mechanically accept utensils 110 and be smoked therewith. For example, smoking appliance 90 may be configured as an artificial delivery device for plant extract(s) and/or therapeutic compounds, having a medium (e.g., a particulate or porous medium) that receives utensil(s) 110 mechanically, and may be activated by burning to release the plant extract(s) and/or therapeutic compounds from utensil(s) 110, to be inhaled by the user. In certain embodiments, the medium, and possibly utensil(s) 110, may be configured to burn and/or release the respective the plant extract(s) and/or therapeutic compounds at specified temperatures and under specified conditions that are different from typical tobacco burning conditions, e.g., to enhance the efficiency of delivery of the plant extract(s) and/or therapeutic compounds to the user.

In various embodiments, utensils 110 may be between about 1-15 cm long, wherein the length may depend on the length of smoking appliance 90 into which it is to be inserted. For example, utensils 110 may be prepared at any length and then be trimmable (e.g., by the user, possibly at a blunt end or possibly at a sharp edge thereof) according to the length of smoking appliance 90 before or after insertion thereinto. In various embodiments, utensils 110 may be between about 0.5-3 mm wide, such that is may be easily inserted into a conventional cigarette, avoiding harm or distortion of smoking appliance 90 and allowing regular use thereof.

According to some embodiments, at least one end of the stick-like device has a point, in order to enable the easy insertion thereof into the cigarette. For example, the stick-like device may be shaped similarly to a toothpick, which may or may not be blunt on one side, as long as it is sharp on the other side to ease insertion into the cigarette. For example, if the stick-like device is trimmed before insertion into the cigarette, it may be trimmed at an angle, so as to form a pointed end for insertion.

In various embodiments, utensils 110 may be made of any appropriate material that provide the required mechanical characteristics and allow incorporation of the plant extract. For example, utensils 110 may be made of wood, paper (e.g., hardened paper) or plastics such as polymers, e.g., polysaccharides, with cross-linked plant extract(s). The plant extract(s) may be associated to utensils 110 by various methods, such as immersion, soaking, coating, cross-linking, etc.

For example, in certain embodiments, utensils 110 may be prepared by adding a cannabis oil into a polysaccharide solution; pouring the solution into a mold comprising at least one compartment, the compartment has the size and shape of utensils 110; and chemically hardening or physically curing the solution in the compartment in order to obtain utensils 110. In various embodiments, the mold may comprise two or more compartments, with possibly different compartments differing from each other in shape, size or both. Utensils 110 may further be coated and/or inserted into respective sleeve elements, and aromatic materials, colors, hardening materials and/or curing material(s) may be added to the solution. Hardening methods may include chemical hardening by cross-linking and/or physical hardening by UV (ultraviolet) and/or heat radiation curing. Indications 120 may then be applied (e.g., attached or printed) upon utensils 110.

In certain embodiments, utensils 110 may have inner spaces or compartments (with or without openings) into which the plant extract may be introduced, e.g., by immersion or injection. In certain embodiments, utensils 110 may be made of metal, e.g., having internal compartments or grooves configured to receive and hold the plant extract(s) and release the plant extract(s) upon heating of metal utensil 110 during smoking. In certain embodiments, metal utensils 110 may even be re-usable, e.g., by cleaning them after use and dipping them in plant extracts, as the spaces or grooves therein may be configured to hold a pre-defined amount of plant extract. In certain embodiments, utensils 110 may have a hollow channel through their whole length or through part of their length, e.g., like a borehole, which may receive and/or be filled by the plant extract.

In various embodiments, utensils 110 may comprise the plant extract(s) or the user may introduce selected plant extract(s) into utensil 110, e.g., with utensil 110 configured to receive a pre-defined amount of plant extract. For example, utensil 110 may be provided with the plant extract(s) (e.g., cannabis oil, see below) and may be prepared by the user for smoking, e.g., by soaking or dipping utensil 110 in the plant extract and/or by filling hollow groove(s) or compartment(s) therein. Certain embodiments comprise kits for preparation of utensil 110 by the user (either first-time or in a reusable version of utensil 110), with utensil(s) 110, plant extract(s) and respective instructions.

In certain embodiments, disclosed kits may comprise cannabis-free utensils 110, cannabis oil, instructions for incorporating the cannabis oil into the cannabis-free utensils 110; and optionally means for incorporating the cannabis oil into the cannabis-free utensils 110 (e.g., an appropriately-shaped container, wetting means, etc.).

In certain embodiments, disclosed kits may comprise different kinds of utensils 110, containing different type of plant extract(s) and/or therapeutic compound(s). For example, users may select different types or compositions of plant extract(s) and/or therapeutic compound(s) at different times (e.g., during the day and at the evening), and therefore may use corresponding utensils 110 with different indicated compounds or combinations or amounts of compounds (e.g., having different amounts of THC—tetrahydrocannabinol and CBD—cannabidiol).

According to some embodiments, utensils 110 may be clad (covered or coated) by any appropriate sleeve-like element (not shown) configured to provide the desired physical properties, such as desired shape, strength, rigidity, and the like and/or configured to hold and then release pre-defined amounts of plant extract(s). The sleeve or sleeve-like element may be removable or non-removable from utensil 110.

According to some embodiments, utensils 110 may be made of soft material such as dough that is prepared to have specified shape, strength and resilience that are required for insertion thereof into smoking appliance 90, and into which the plant extract may be incorporated. In certain embodiments, utensils 110 may be configured to be very thin, flexible or flakey—to be used in hand-rolled cigarettes or in pipes. The amount of used utensil 110 may be related to the amount of released plant extract by diverse indications.

In various embodiments, the plant extract may comprise a cannabis extract and/or oil. Indications 120 may comprise indication(s) 121 for a THC content or level, and/or indications(s) 122 for predominant component(s) of the cannabis extract and/or oil, such as other cannabinoids, terpenes, terpenoids, or aromas (see non-limiting example in FIG. 2). Other possible plant extract(s), usable in utensils 110 and/or as additions to the cannabis extract, comprise any plant extract or oil, various terpenes or terpenoids, or any other plant extract or releasable compound. For example, any of menthol, pine oil, clove oil, eucalyptus oil, orange oil, lemon oil, or other essential oils, as well as flavor essences (e.g., lemon flavor, bubble gum flavor, enhanced cannabis flavors) may be included in utensil 110.

For example, in some embodiments, utensils 110 may comprise condensed cannabis oil in a matrix configured to endow the product with the right rigidity, e.g., make it tooth-pick-like, so that it can be easily inserted to any existing cigarette, burns at the same rate as the cigarette, and leave no particles and minimum ash, while providing the cannabis oil or its products to the user. Utensils 110 may be provided at a range of different concentrations of CBD, THC, CBG (cannabigerol), CBN (Cannabinol) and with different aromas and/or odors (e.g., mint, lemon, orange)—which are indicated, e.g., by color code(s) on each utensil 110.

It is noted that terpenoids are naturally occurring hydrocarbons produced by a wide variety of plants and animals. Terpenoids are classified based on five-carbon (isoprene) units as their building blocks, numbering more than 55,000 molecules having been discovered, and may be used in different combinations in disclosed embodiments. Different terpenes include hemiterpenes (C5), monoterpenes (C10), sesquiterpenes (C15), diterpenes (C20), sesterterpenes (C25), triterpenes (C30), and polyterpenes (>C30). Diverse functional roles of terpenoids have been critically studied and well-accepted now. Most comprehensively studied of which is the effect of terpenes in prevention and treatment of cancer. Illustratively, taxol derivatives (paclitaxel and docetaxel) are among the widely used drugs in cancer chemotherapy. Other important therapeutic uses of terpenoids include antimicrobial, antifungal, antiviral, antihyperglycemic, anti-inflammatory, antioxidants, antiparasitic, immunomodulatory, and as skin permeation enhancer.

It is noted that disclosed aromas may comprise any of a range of aromatics, which contain many volatile and fragrance organic molecules, classified as esters, linear terpenes, cyclic terpenes, aromatic, amines, etc. At room temperature, most of the aromatics are liquids (usually oils) but they can be also in gas or even in solid-state (e.g., vanillin, camphor, and menthol). As aroma molecules are typically very sensitive to light, oxygen, humidity, and high temperatures, certain embodiments are configured to protect aromas, e.g., within the matrix structure and/or utensil 110. Aromas may further include flavors, which comprise reactive components with varying solubility and partition coefficients in the oil and water phases. The vapor pressure values are an important characteristic of aromas since they provide a method for ranking the relative volatilities of the compound. The partition coefficient (log P [o/w]) is another important parameter as the underlying principle that governs the release of flavors from the food matrix into the gas phase. For example, certain embodiments comprise aromatic coating methods for preparation of the sticks as utensils 110—which use a combination of maltodextrins and cyclodextrins to preserve and stabilize the aromas in utensils 110.

In certain embodiments, the matrix may be configured to burn at a rate similar to the burning rate of tobacco or other carrier material in the cigarette or in the smoking appliance. The matrix may be used as utensil 110 or as part thereof, and may be thin (e.g., 1 mm in diameter or less) and resistant to breaking (e.g., stiff or slightly flexible). The matrix may be configured to be straight and burn without leaving any residue behind.

In various embodiments, the extracts and/or added terpenes, terpenoids and/or added aromas may be applied onto utensil 110 by any of the following procedures: (i) coating or impregnating utensil 110 with, e.g., terpenes or terpenoids, possibly within specified formulations, (ii) spraying terpenes or other compounds upon utensil 110, (iii) using a powder as carrier for terpenes (and/or extracts and/or other essences) and mixing the powder in the matrix and/or coating of utensil 110, (iv) using terpene emulsions, e.g., based on Pickering emulsions or related compounds to infuse utensil 110, and/or (v) protective terpenes in the matrix if the matrix is heat-pressed, to prevent modifications or disintegration of the terpenes. In certain embodiments, extracts, oils, terpenes, terpenoids and/or aromas may be applied onto utensil 110 in form of a paste. Concerning (iv), it is noted that terpene emulsions may be employed in the formulation of Pickering emulsions (similar to or in conjunction with other biological and food-grade particles) due to their excellent biocompatibility, biodegradability, as well as attractive potential applications. Among them, starch, zein, soy protein, whey protein, and bacteria-related particles may serve as Pickering emulsifiers in various embodiments.

Certain embodiments comprise packaged set(s) 130 including a plurality of utensils 110 which may differ with respect to the at least one compound and the corresponding indications 120, as exemplified schematically in FIG. 3. Complementary compositions of the plant extracts may be provided in each set (e.g., ones with little THC and much CBD and ones with much CBD and little THC). In certain embodiments, utensils 110 may be configured to allow insertion of more than one utensil 110 at a time into smoking appliance 90, e.g., utensils may be configured as thin spikes that can be inserted into cigars, or as rollable threads with color indications, and the user may select a few utensils 110 having a required combination of the plant extracts for each use (smoking) of smoking appliance 90. In certain embodiments, such thin utensils 110 may comprise means for interconnecting multiple utensils 110 to make their insertion into smoking appliance 90, e.g., grooves or nooks may be used to attach utensils 110 to each other and enhance their longitudinal structural stability upon insertion.

For example, packaged set 130 of utensils 110 may have cannabis extracts and/or oils having different levels of THC and/or different levels of other cannabinoids and/or of other components (e.g., terpenes, terpenoids) or characteristics (e.g., aromas) with corresponding indications 120, as illustrated schematically in FIG. 3.

The contents of the cannabis oil incorporated into utensils 110, and the ratios between the active ingredients found therein, may be determined according to any known protocols. Therefore, many types of utensils 110 may be prepared, each having a specific, predefined content and ratio of active ingredients, in particular CBD and THC. The various types of utensils 110 may be labeled according to their content, e.g., by size, color code, shape, labels and the like as indications 120. In a non-limiting example, the ratio between CBD and THC may be 10:1, utensils 110 may weigh about 100-150 mg and may correspondingly contain about 20-60 mg of CBD, 2-6 mg of THC, as well as additional supporting and hardening materials. According to some embodiments, utensils 110 may comprise any of about 20, 25, 30, 35, 40, 45, 50, 55 or 60 mg of CBD. According to some embodiments, utensils 110 may comprise any of about 2.0, 2.5, 3.0, 3.5, 4.0, 4.5, 5.0, 5.5 or 6.0 mg THC.

In case utensils 110 comprise polymer(s) to which the cannabis oil is cross-linked, the cross linking may be performed using various cross-linking methods and materials. For example, the cross-linking may be performed using microbial poly(gamma-glutamic acid) (PGA) with polysaccharides and the cannabis oil, which may be cross-liked as well or incorporated into the cross-linked product of the PGA and the polysaccharide. For example, the cross linking may be performed by using polylactic acid (PLA), including poly(L)lactide (PLLA) and poly(D)lactide (PLDA). For example, the cross linking may be performed using any appropriate cross-linkable composite, for example a composite prepared from poly(ethylene glycol) dimethyl ether (PEGDE)-500, $LiClO_4$, fumed silica and about 10% wt methyl, butyl or octyl methacrylate. For example, the cross linking may be performed using any appropriate polysaccharide. For example, the cross linking may be performed by pre-chemically treating the cannabis oil using thiol-ene addition reactions, azide-alkyne cyclo-addition reactions, Diels-Alder reactions and the like, wherein the formed adduct oil products are then cross-linked. The cannabis oil may also be pre-treated using triazolinediones (TADs), such as 4-phenyl-1,2,4-triazoline-3,5-dione and subsequently cross-linked. In any of the embodiments, the cross-linking mechanism may be selected to avoid releasing toxic fumes when utensil 110 in smoking appliance 90 is smoked. In various embodiments, the material from which utensil 110 is prepared may be non-toxic and combustible, thereby providing a utensil that may burn together with the cigarette, while releasing carbonized plant extracts (e.g., cannabis oil), without having an intoxication effect on the user. The combustion rate of the stick-like device may be similar to that of a conventional cigarette.

In various embodiments, utensils 110 may further comprise additives such as coloring and flavoring products, as well as enhancers, such as cocoa solids, licorice, tobacco extracts, and various sugars, and possibly perfume-like flavor(s)/fragrance(s)—any of which may be incorporated in utensils 110 as additional plant extracts and/or as additives. In various embodiments, utensils 110 may be coated by a material that contains aromatic elements, possibly one or more plant extracts.

Advantageously, disclosed systems 100 and utensils 110 provide well-measured amounts of plant extracts that can be easily specified and controlled. Particularly in case of cannabis oils, disclosed systems 100, utensils 110 and methods 150 disclosed below—provide a reliable way of consuming cannabis oils and components thereof in a highly controllable and standardized methods. Indications 120 are further configured to clearly indicate the compounds to be smoked, and allow the user to select the required composition for any smoke.

Advantageously, disclosed systems 100 and utensils 110 provide active materials at pre-defined and known dosage, which is required e.g., in regulation procedures for medical use of cannabis and/or other plant extracts and/or any therapeutic compound. The amount of any of the active materials (e.g., cannabinoids) may be pre-defined and clearly indicated on utensil 110 and thus allow for regulated medical use thereof—through smoking which may be the preferred administration method for many patients and moreover has been proved to have high efficiency in this respect. For example, therapeutic compounds that target the brain, pass the blood brain barrier with higher efficiency when inhaled, and may be administered using systems 100 and utensils 110. In certain embodiments, utensil 110 and/or therapeutic compounds therewithin may be configured to further enhance the bioavailability of the latter by the heating and/or carbonization thereof during the administration process.

Advantageously, disclosed systems 100 and utensils 110 may be used with the therapeutic compound(s) to provide new ways of administering drugs that can be inhaled and are not damaged (or possibly modified favorably) by the smoking procedure.

Additional advantages include simple handling of utensils 110 (do not require rolling), simpler regulation compared to cannabis inflorescences due to the known and controlled amounts of THC or any other cannabinoid (e.g., CBD, CBN (Cannabinol), CBG, etc.) or any other compound (e.g., terpenes, terpenoids) in case of using cannabis extract or oil, consistent and repeatable smoking experience, and brand building possibilities due to the repeatability of the experience.

Moreover, utensils 110 may be used to deliver various plant extracts and possibly even therapeutic drugs or compounds that can be inhaled after heating and/or carbonizing during smoking.

FIG. 4 is a high-level flowchart illustrating a method 150 of administering a plant extract or any compound at a controlled amount, according to some embodiments of the invention. The method stages may be carried out with respect to systems 100 and utensils 110 described above, which may optionally be configured to implement method 150. Method 150 may comprise the following stages, irrespective of their order.

Method 150 may comprise administering plant extract(s) at a controlled amount (stage 152) by applying the plant extract(s) to utensil(s) designed to be inserted into a smoking appliance (stage 155), indicating at least one compound that is included in the plant extract(s) on the utensil(s) (stage 160), and using the smoking appliance to inhale the plant extract(s) from the utensil(s) inserted therewithin (stage 170).

In certain embodiments, method 150 may comprise administering at least one therapeutic compound at a controlled amount (stage 153) by applying the at least one therapeutic compound to utensil(s) designed to be inserted into a smoking appliance (stage 155) and using the smoking appliance to inhale the therapeutic compound(s) from the utensil(s) inserted therewithin (stage 170).

In certain embodiments, method 150 may further comprise designing the utensil(s) to be inserted into the smoking appliance (stage 157), e.g., by sticking or pushing the utensil into the smoking appliance. For example, the smoking appliance may be a cigarette and the utensil may be made as a stick that is thinner than the cigarette and has a sharp end configured to be inserted into tobacco of the cigarette throughout at least some, or possibly most, of a length of the cigarette (stage 158). Corresponding embodiments may be applicable to cigars or other smoking appliances such as pipes, hand-rolled cigarettes, bongs etc.

In certain embodiments, method 150 may further comprise providing a plurality of utensils with different levels of the indicated at least one compound and/or with different combinations of the therapeutic compound(s) (stage 180).

For example, the plant extract(s) may comprise cannabis extract(s) and/or oil(s), and/or essential plant oils. Method 150 may further comprise indicating a THC level, predominant components (e.g., cannabinoids, terpenes) and/or characteristics (e.g., aromas) of the cannabis extract and/or oil (stage 182). Method 150 may further comprise providing a plurality of utensils with different levels of THC and/or with different predominant components and/or characteristics (stage 185).

Figure 5:
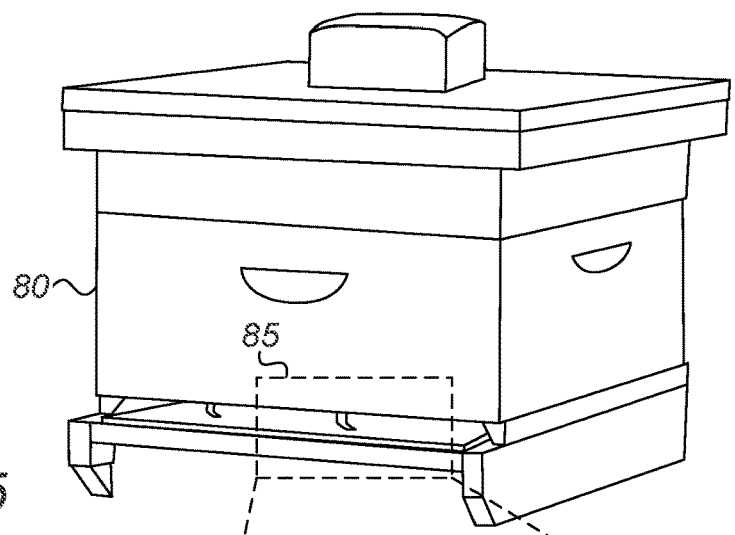
FIGS. 5 and 6 are schematic illustrations of systems having beehives configured to provide complexes of honey and plant extracts, according to some embodiments of the invention.
Figure 6:
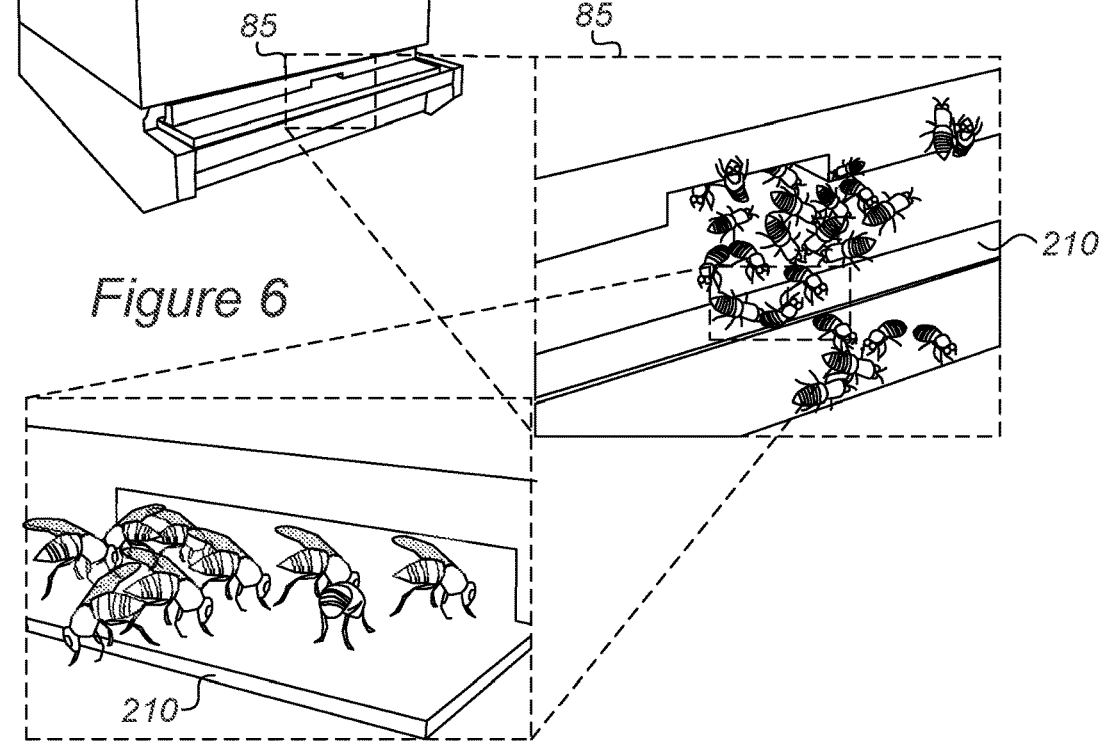

FIGS. 5 and 6 are schematic illustrations of systems 200 having beehives 80 configured to provide complexes of honey and plant extracts and/or therapeutic compound(s), according to some embodiments of the invention. Systems 200 may comprise beehives 80 having substrate(s) 210 infused with plant extract(s) and/or therapeutic compound(s)—that are attachable onto at least one hive region 85 that is stepped on by bees, wherein substrate(s) 210 are configured to soil bees that step thereon with the plant extract and/or the therapeutic compound(s). For example, substrate(s) 210 such as pads (made e.g., of sponge or foam) soaked by the plant extract(s) and/or the therapeutic compound(s), may be attached to entrance(s) to hive 80 and may have any corresponding shape (see, e.g., in FIGS. 5 and 6, the openings and corresponding substrates 210 may be straight or round, narrow or broad, etc.).

Advantageously, bees stepping on substrate 210 and being soiled by the plant extract(s) and/or the therapeutic compound(s) may then mix the plant extracts, intentionally or unintentionally, in the produced honey to yield a complex of honey and the plant extracts and/or therapeutic compound(s), which is not achievable by other means (such as mixing prepared honey with plant extracts and/or therapeutic compounds).

For example, the plant extracts may comprise cannabis extract and/or oil, to yield a complex of honey and cannabis that is not achievable by other means, as the complexes may include bonds between the honey and the plant extracts that are formed during the honey processing by the bees. The cannabis in the cannabis-honey complex may be incorporated into the honey during the honey's preparation process by the bees from pollen. According to some embodiments, the cannabis-honey complex may have a unique HPLC (High Pressure/Performance Liquid Chromatography) pattern, different from other types of honey and/or other types of cannabis. According to some embodiments, the HPLC fingerprint of the cannabis-honey complex is unique in comparison to other types of honey and/or other types of cannabis.

In certain embodiments, beehive 80 may be designed to cause at least one part of the body of the bees entering beehive 80 to touch at least part of substrate 210 at entrance 85. For example, regions 85 may be configured to cause bees contact substrate 210 with cannabis oil with their bodies, e.g., legs, abdomen and/or thorax, while entering beehive 80. The thus soiled bees may be at least partly coated or stained with cannabis oil, which they may then take with them into beehive 80 and possibly mix with honey to yield the cannabis-honey complex during the honey-preparation process. According to some embodiments, beehive 80 may be designed to induce contact of entering bees with substrate 210. For example, the diameter or width of the entrance 85 to beehive 80 may be restricted, so that at least on one of its dimensions is between about 0.3-1.0 cm and thereby induce contact between the bee and substrate 210.

In certain embodiments, in addition or alternatively to using substrate 210, smoke of carbonized cannabis oil may be distributed onto and/or in the surroundings of beehive 80, exposing the bees and/or beehive 80 to carbonized cannabis, which may then be incorporated into the honey to yield the cannabis-honey complex.

In certain embodiments, in addition or alternatively to using substrate 210, cannabis oil may be sprayed onto the internal elements of beehive 80, enhancing the incorporation of the cannabis oil by the bees into the cannabis-honey complex.

Advantageously, disclosed cannabis-honey complexes and/or complexes of honey and therapeutic compound(s)—may have enhanced therapeutic effects, with respect to either honey alone, cannabis alone, and therapeutic compound(s) alone, or mechanical mixtures thereof. The preparation process of the cannabis-honey complex by the bees may induce additional beneficial properties to the disclosed products. Examples for such properties include therapeutic and/or recreational effects. Moreover, as administration method, cannabis-honey complexes may be more effective and/or more becoming than other methods of cannabis administration.

Certain embodiments comprise processes of preparing new complexes of honey and therapeutic compound(s) through the disclosed methods and systems of soiling bees with the therapeutic compound(s) and letting the bees integrate the therapeutic compound(s) into the honey.

Figure 7:
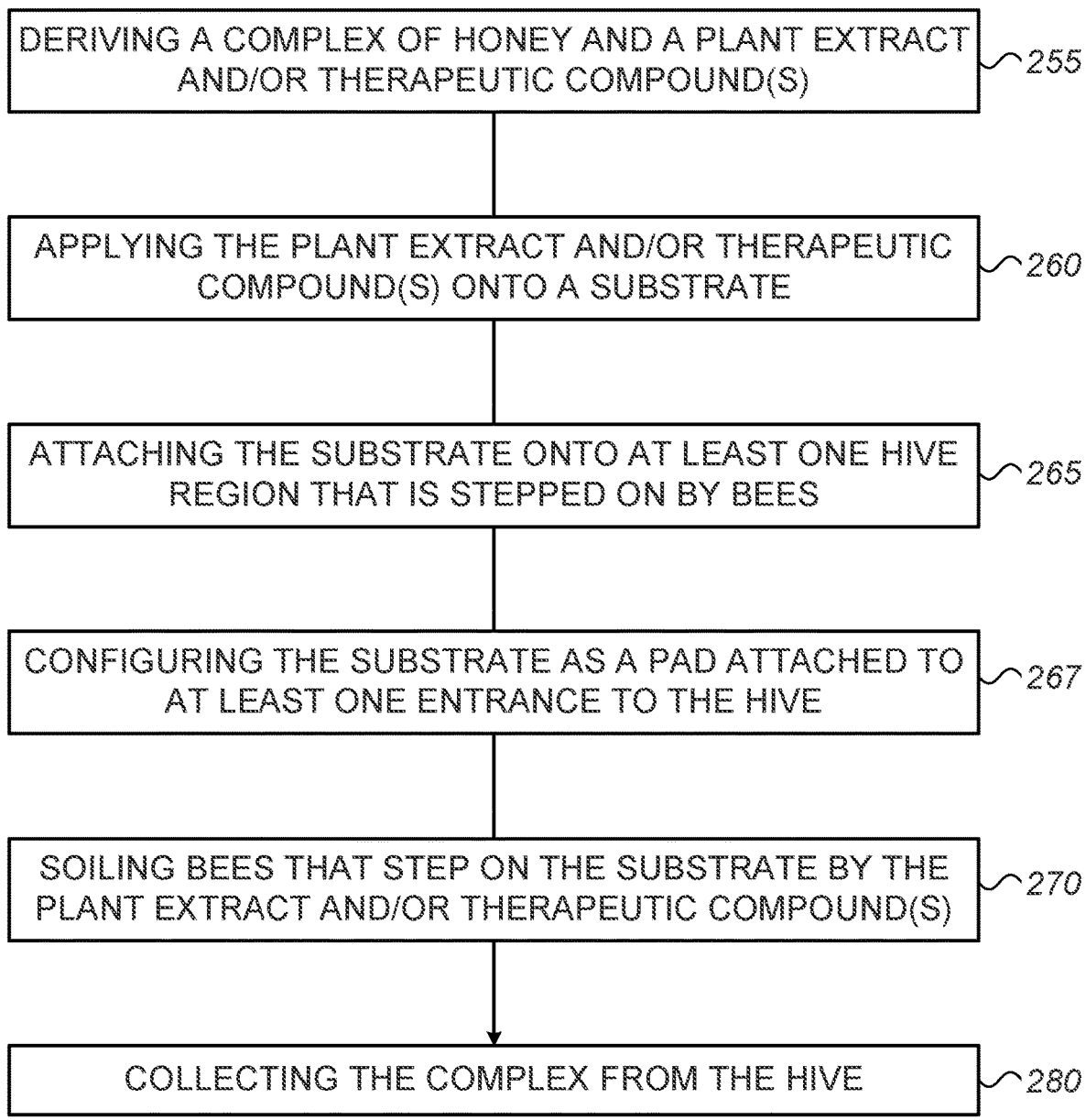
FIG. 7 is a high-level flowchart illustrating a method of deriving a complex of honey and plant extract(s) and/or therapeutic compound(s), according to some embodiments of the invention.

FIG. 7 is a high-level flowchart illustrating a method 250 of deriving a complex of honey and plant extract(s) and/or therapeutic compound(s), according to some embodiments of the invention. The method stages may be carried out with respect to systems 200 described above, which may optionally be configured to implement method 250. Method 250 may comprise the following stages, irrespective of their order.

Method 250 comprises deriving a complex of honey and one or more plant extract and/or therapeutic compound(s) (stage 255) by applying the plant extract and/or therapeutic compound(s) onto a substrate (stage 260) and attaching the substrate onto at least one hive region that is stepped on by bees (stage 265). Applying 260 and the substrate are configured to soil bees that step on the substrate with the plant extract and/or therapeutic compound(s) (stage 270), method 250 further comprises collecting the complex from the hive (stage 280). Method 250 may further comprise configuring the substrate as one or more pads attached to at least one entrance to the hive (stage 267). The pads may be shaped according to the corresponding shape of the openings in the hives, e.g., straight or round, narrow or broad, etc.

For example, the plant extract may comprise cannabis extract and/or oil, and disclosed method 250 may provide an efficient way of complexing cannabis extract and/or components thereof with honey.

In some embodiments, systems 200 and/or methods 250 may be configured to produce complexes of honey and therapeutic compound(s) that may be used as new therapeutic compounds having new therapeutic effects.

It is noted that a value modified by the term "about" is understood to encompass±10% of the value.

In the above description, an embodiment is an example or implementation of the invention. The various appearances of "one embodiment", "an embodiment", "certain embodiments" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention may also be implemented in a single embodiment. Certain embodiments of the invention may include features from different embodiments disclosed above, and certain embodiments may incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. A method of administering complexes of honey and *cannabis* extracts at a standardized and controlled amount, the method comprising:
    applying a complex of honey and *cannabis* extract to a utensil that is designed to be inserted into a smoking appliance,
    indicating, on the utensil, amounts of cannabinoids, terpenes, or terpenoids that is included in the *cannabis* extract, and
    using the smoking appliance to inhale the complex of honey and *cannabis* extract from the utensil inserted therewithin,
thereby administering a specified ratio of compounds and concentrations or amounts thereof.

2. The method of claim 1, further comprising designing the utensil to be inserted into the smoking appliance by sticking.

3. The method of claim 1, wherein the smoking appliance is a cigarette and the utensil is a stick that is thinner than the cigarette and has a sharp end configured to be inserted into tobacco of the cigarette throughout at least some of a length of the cigarette.

4. The method of claim 1, further comprising providing a plurality of utensils with different levels of the indicated amounts of cannabinoids, terpenes, or terpenoids.

5. The method of claim 1, wherein the indicating comprises indicating a THC (tetrahydrocannabinol) level and at least one additional predominant component of the *cannabis* extract.

6. The method of claim 5, further comprising providing a plurality of utensils with different levels of THC and/or utensil with different predominant terpenes or terpenoids.

* * * * *